United States Patent [19]

Cunningham

[11] 4,379,472
[45] Apr. 12, 1983

[54] MAINTAINING THE DIMENSIONAL INTEGRITY OF THERMOPLASTIC TUBING ENDS FOR RECEIVING A LUER

[75] Inventor: Joel Cunningham, Del Mar, Calif.

[73] Assignee: Baxter Travenol Laboratories, Inc., Deerfield, Ill.

[21] Appl. No.: 282,908

[22] Filed: Jul. 13, 1981

Related U.S. Application Data

[62] Division of Ser. No. 110,261, Jan. 7, 1980, Pat. No. 4,297,316.

[51] Int. Cl.³ .............................................. F16L 55/10
[52] U.S. Cl. .................................. 138/89; 138/96 R; 422/40
[58] Field of Search ................... 138/89, 96 R; 422/1, 422/25, 26, 117, 118, 40

[56] References Cited

U.S. PATENT DOCUMENTS

| | | |
|---|---|---|
| 244,356 | 5/1977 | Pardo . |
| 2,629,148 | 2/1963 | Kollsman . |
| 2,802,716 | 8/1957 | Cutter . |
| 3,307,552 | 3/1967 | Strawn . |
| 3,610,288 | 10/1971 | Carr ................................. 138/96 R |
| 3,744,528 | 7/1973 | Vestal ........................... 138/96 R X |
| 3,918,450 | 11/1975 | Patel . |
| 3,948,290 | 4/1976 | Arisland ....................... 138/96 R X |
| 3,977,403 | 8/1976 | Patel . |
| 3,987,930 | 10/1976 | Fuson ............................... 138/89 X |
| 4,057,050 | 11/1977 | Sarstedt . |

Primary Examiner—James E. Bryant, III
Attorney, Agent, or Firm—Paul C. Flattery; Daniel D. Ryan; Garrettson Ellis

[57] ABSTRACT

An end of thermoplastic tubing which is exposed to a temperature capable of causing dimensional distortion of the tubing end may be maintained by enclosing the tubing end with a tubular end cap. The end cap defines an inner member projecting axially into the bore of the tubing end, with the inner member defining an outer diameter of essentially the diameter of the bore of the tubing end, so that the dimensional integrity of the tubing end is maintained during the heating step to thereafter sealingly receive a luer.

2 Claims, 3 Drawing Figures

MAINTAINING THE DIMENSIONAL INTEGRITY OF THERMOPLASTIC TUBING ENDS FOR RECEIVING A LUER

This is a division of application Ser. No. 110,261, filed Jan. 7, 1980, now U.S. Pat. No. 4,297,316.

BACKGROUND OF THE INVENTION

The great majority of sets for the administration of parenteral solution, blood, plasma, or the like, in medical use contains an ester-type plasticizer to soften the vinyl. While this plastic material has many advantages for use in sets of this type, as well as non-medical devices involving plastic tubing, it has suffered a drawback that has made it undesirable to steam sterilize the plastic set. The reason for this is that polyvinyl chloride plastic generally can undergo dimensional distortion at steam sterilizing temperatures of 121° C. and the like. This, in turn, can cause the significant disadvantage that a luer type connection site may be spoiled by the warpage of dimensional distortion which can take place upon steam sterilization. A luer connector is a tapered hollow tubing which fits into a correspondingly sized socket of a luer adaptor, to provide a tight, aseptic seal. Many conventional administration sets utilize this type of connection.

As the result of this, manufacturers have been forced to sterilize many of the administration sets of polyvinyl chloride or other heat-distortable plastics with ethylene-oxide or, alternatively, some other low heat technique such as radiation sterilization, since the desirable and inexpensive luer adaptor connection site has not been successfully maintained in its proper dimensions for effective sealing under steam sterilization.

In accordance with this invention, the dimensional integrity of an end of thermoplastic tubing may be maintained at temperatures which are capable of causing dimensional distortion of the tubing end. As a result of this, commercial medical administration sets may be steam-sterilized in such circumstances where that it is desirable, without compromising the quality of luer adaptor sites on the sets, which otherwise could be warped by the temperatures encountered in the steam sterilization process. This opens up further significant economies in the mass production of medical administration and other sets to reduce the cost of their manufacture, while maintaining high reliability for aseptic connection with other units.

DESCRIPTION OF THE INVENTION

In accordance with this invention, a method is provided for maintaining the dimensional integrity of an end of thermoplastic tubing which is exposed to a temperature capable of causing dimensional distortion of the tubing end. In this invention, the tubing end is enclosed during the temperature exposure with a tubular end cap. The end cap defines an inner member projecting axially into the bore of the tubing end, with at least an end-engaging portion of the inner member defining an outer diameter of essentially the diameter of the bore of said tubing end.

As the result of this, during the heating step which would otherwise be capable of causing dimensional distortion of the tubing end, the tubing end, and particularly its inner diameter region, is prevented from distortion by the retentive action which is provided by the end cap throughout the temperature exposure.

Preferably, the tubular end cap is made of an elastomer which resists melting and physical degradation at the temperature of use. Natural rubber latex or other thermoset elastomers are generally preferred for use, particularly in which the end cap defines an outer end wall sealing the tubing end, and a laterally-positioned pull tab to facilitate removal of the end cap.

It is also preferable for the inner diameter of the tubular end cap to be slightly less than the outer diameter of the tubing end, for firm, elastic retention thereof.

As the result of this, the end of the tubing may retain its desired proportions, so that after cooling the end cap may be removed when use is desired, and the tubing end retains its proportions for sealingly receiving a luer connector, the predetermined transverse dimensions of the bore of the tubing end permitting luer connectors of predetermined size to thereafter fit therein.

Figure 1:
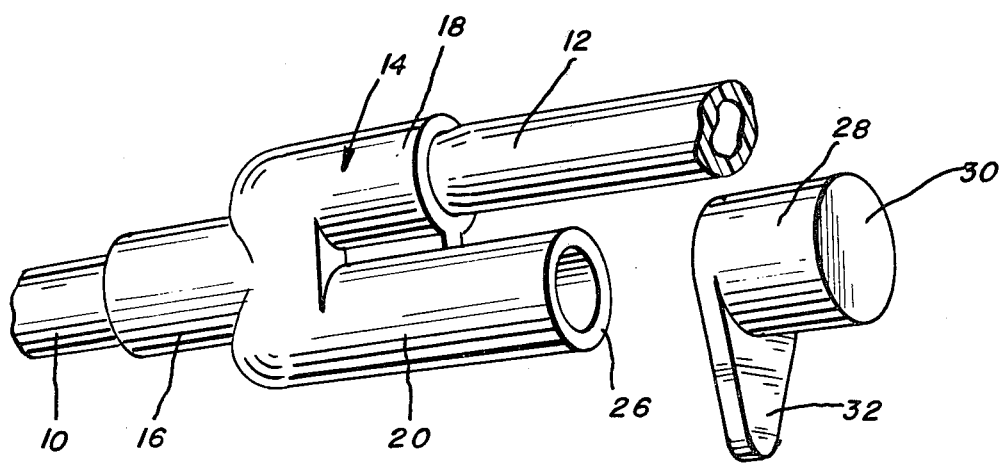
FIG. 1 is a fragmentary, perspective view of a portion of a medical fluid administration set utilizing a luer connector in accordance with this invention.
Figure 2:
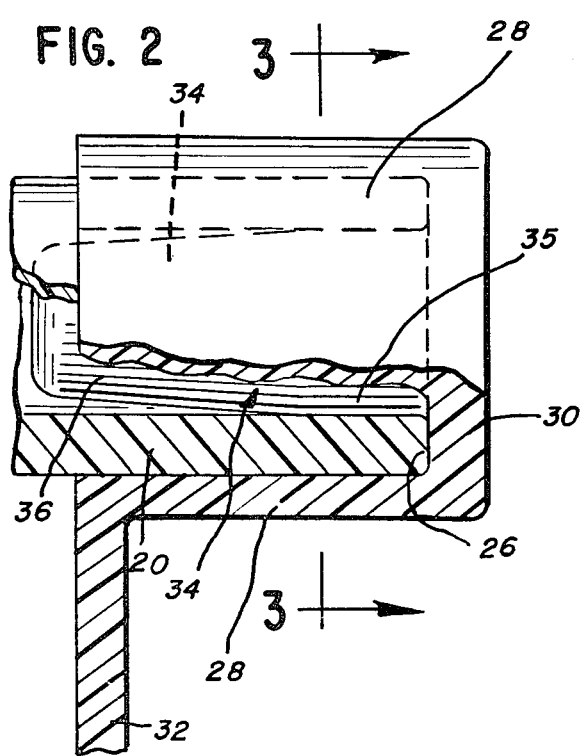
FIG. 2 is an enlarged, fragmentary elevational view, taken partly in transverse section, of the luer adaptor in accordance with this invention carrying an end cap.
Figure 3:
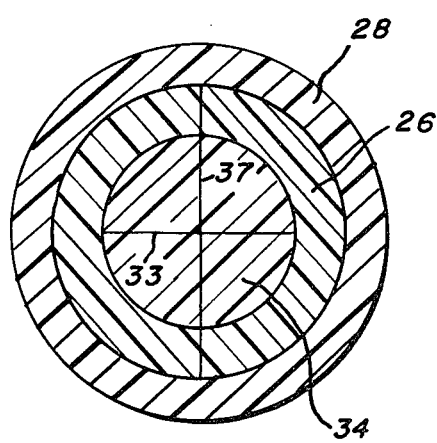
FIG. 3 is a sectional view taken along lines 3—3 of FIG. 2.

Referring to the drawings, thermoplastic tubing 10, 12 is shown to be part of a medical blood, plasma, or solution administration set of any desired design.

Positioned between tubing sections 10 and 12 is a molded Y-connector 14 to provide an intermediate access site between the ends of the administration set. All of the members 10, 12, and 14 may be made of polyvinyl chloride plastic, for example, or another thermoplastic material which has a heat distortion temperature below the temperature it is intended to be sterilized or otherwise heat-treated at.

Y-connector 14, as shown, comprises three interconnected tubular ports 16, 18, 20, with port 16 receiving tubing 10, and port 18 receiving tubing 12, the tubings being preferably solvent-sealed into the apertures 16, 18.

Port or tubing 20 of the Y-connector is open, and defines a luer adaptor, being adapted to receive a luer connector, which in turn may be sealingly connected at one end to a length of tubing which may be part of a second medical fluid administration set or other conduit member which is intended for connection at tubing end 20 at some time during the course of use of the respective set. For example, a connection between a pair of solution administration sets as shown in U.S. Pat. No. 4,105,029 may be made by a luer connection utilizing this present invention, similar to the CONTINU-FLO and the ADD-A-LINE solution administration sets which are sold by Travenol Laboratories, Inc. of Deerfield, Ill. Also, this invention may be used on a set designed for plasmapheresis.

In accordance with this invention, prior to the steam sterilization or other heat treatment step, the end 26 of tubing 20 is enclosed with tubular end cap 28, which preferably is made of a latex material which is thermosetting in nature, and thus does not distort dimensionally to any significant degree during the heating step. End cap 28 defines an outer end wall 30 which closes the end 26 of tubing 20, to seal the tubing end during the sterilization. Furthermore, a laterally-positioned pull tab 32 may be provided to facilitate removal of the end cap when desired.

In accordance with this invention, end cap 28 defines, projecting inwardly from end wall 30, an inner member 34 projecting axially into the bore of tubing end 26. Inner member 34 defines, at at least its end-engaging portion 35, an outer diameter 33 of essentially the diameter of the bore of tubing end 26. As the result of this, the retentive action of inner member 34, preferably coupled with the added retentive action provided by the remainder of tubular end cap 28, retains tubing end 26 in the desired dimensional configuration throughout the steam sterilization process or other desired heat treatment step.

Inner member 34 also defines a tapered portion 36 to facilitate insertion into tubular port 20.

It is also preferable for the inner diameter 37 of tubular end cap 28 to be slightly less than the outer diameter of tubing end 26, so that the end cap slightly compresses the tubing end inwardly against inner member 34. This permits the firm retention of the end cap on the tubing end, while at the same time facilitating the maintenance of the dimensional integrity of the inner diameter of the bore of tubing end 26.

Accordingly, after the steam sterilization process has been completed, the set in accordance with this invention is cooled. Thereafter, it is ready for use simply by manual removal of end cap 28, following which it may be connected with a tubing of another set by sliding a luer connector attached to the other set into the bore of tubing end 26. The maintained dimensional integrity of the bore of the tubing end 26 permits the reliable aseptic connection between end 26 and a luer, despite the steam sterilization or other heat treatment step.

The above has been offered for illustrative purposes only, and is not intended to limit the invention of this application, which is as defined in the claims below.

That which is claimed is:

1. A heat sterilizable, sealed tubing assembly comprising
    a length of thermoplastic tubing having an exterior portion with a normal exterior diameter and an interior bore with a normal interior diameter which undergoes dimensional distortion at a temperature sufficient to effect heat sterilization thereof, and
    an end cap removably engageable on the end of said tubing, said end cap being made of a thermosetting material and including
        exterior wall means defining an end wall operative for engagement against the tubing end to seal the interior portin of the tubing from communication with the atmosphere during heat sterilization,
        'first interior wall means connected to said exterior walls means and defining an inner member which extends inwardly from said end wall into and axially along the interior bore of the tubing and which has an outer diameter generally equal to the interior diameter of the tubing bore for supporting the interior portion of the tubing at its normal diameter during heat sterilization, and
        second interior wall means connected to said exterior wall means and extending from said end wall outwardly radially spaced from said first interior wall means and having an interior diameter less than the exterior diameter of the tubing for compressing the exterior portion of the tubing radially inwardly toward said first interior wall means during heat sterilization.

2. A heat sterilizable, sealed tubing assembly according to claim 1
    wherein said end cap further includes tab means for facilitating removal of said end cap from said tubing end after heat sterilization.

* * * * *